United States Patent [19]

Dutcher et al.

[11] 4,253,462

[45] Mar. 3, 1981

[54] STYLET

[75] Inventors: Robert G. Dutcher, Columbia Heights; Edward G. O'Neill, St. Paul; Richard D. Sandstrom, Scandia, all of Minn.

[73] Assignee: Medtronic, Inc., Minneapolis, Minn.

[21] Appl. No.: 64,947

[22] Filed: Aug. 9, 1979

[51] Int. Cl.³ ............................................. A61B 17/00
[52] U.S. Cl. .............................. 128/303 R; 128/784; 128/DIG. 9
[58] Field of Search ............................... 128/784–786, 128/642, 772, 214.4, 348, 419 P, DIG. 9, 303 R

[56] References Cited

U.S. PATENT DOCUMENTS

| | | | |
|---|---|---|---|
| 3,416,533 | 12/1968 | Fisher et al. | 128/786 |
| 3,572,333 | 3/1971 | Hubert | 128/348 X |
| 4,046,151 | 9/1977 | Rose | 128/785 |
| 4,103,690 | 8/1978 | Harris | 128/785 |
| 4,114,626 | 9/1978 | Beran | 128/348 |
| 4,142,531 | 3/1979 | Magovern et al. | 128/419 P X |

Primary Examiner—Lee S. Cohen
Attorney, Agent, or Firm—John L. Rooney; Joseph F. Breimayer; Lew Schwartz

[57] ABSTRACT

Stylet including a stylet knob, a stylet wire, and a swaged stylet wire retaining sleeve over the stylet wire which engages within the stylet knob providing for controlled length and straightness of the stylet wire and mating within the long thin walled stylet knob.

4 Claims, 3 Drawing Figures

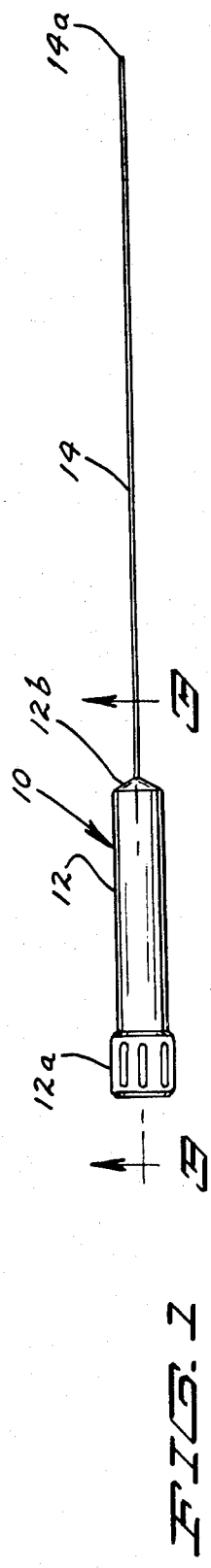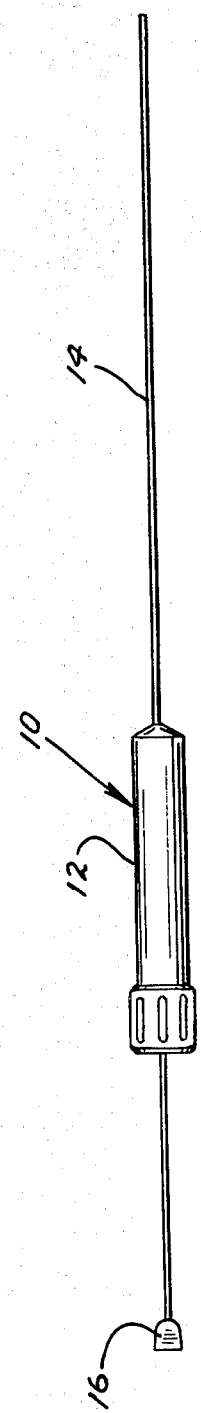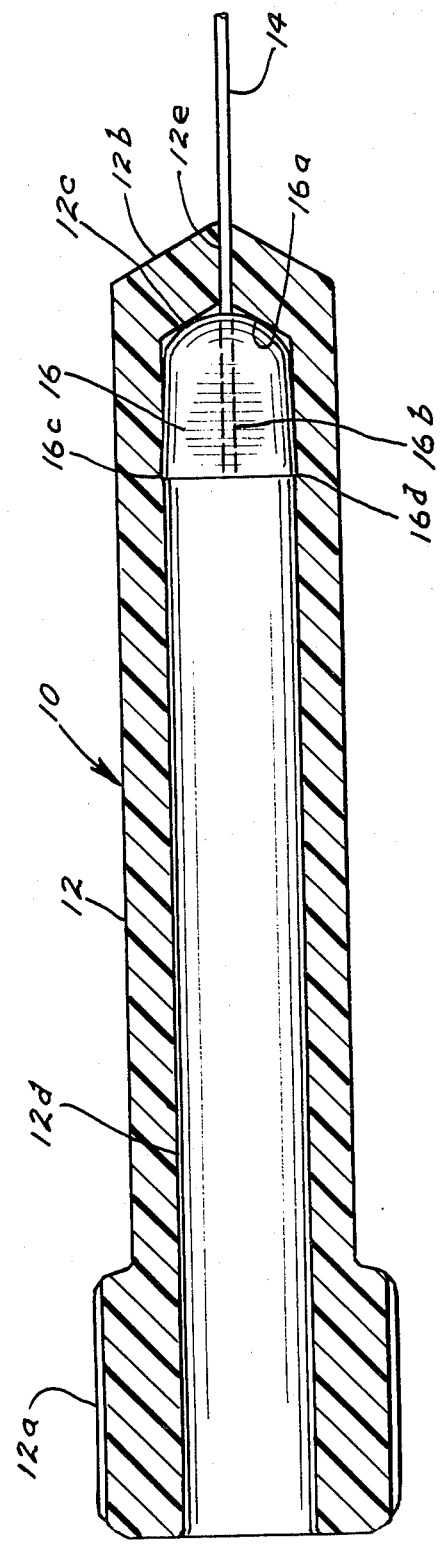

STYLET

CROSS REFERENCE TO CO-PENDING APPLICATIONS

None.

BACKGROUND OF THE INVENTION

1. Field of the Invention

The present invention relates generally to a surgical instrument, and more particularly, pertains to a stylet for use with a pacing lead during insertion of the pacing lead.

2. Description of the Prior Art

The manufacturing of stylets has been plagued with the problems of controlling length of the stylet wire during the manufacture and straightness of the stylet wire as the stylet wire exits the end of the stylet knob. The prior art stylets, during manufacture, have not always had consistent length or straightness resulting in additional manufacturing steps along with added expense in providing a straight stylet wire. More importantly though, the stylet wires after manufacture were not always straight which defeated the purpose of the stylet.

The present invention overcomes the disadvantages of the prior art by providing a stylet having controlled stylet wire length, a straight stylet wire, and easiness of manufacture.

SUMMARY OF THE INVENTION

The present invention provides a stylet wire which is easy to manufacture with controlled length during manufacture, and results in a stylet having a straight stylet wire.

According to one embodiment of the present invention, there is provided a stylet including a thin walled stylet knob having an outer ribbed portion, a tapered outer end, a longitudinal hole running throughout a portion of the stylet knob, a smaller hole running through the tip of the stylet knob, an inner end joining the longitudinal hole to the stylet hole, a stylet wire, and a stylet wire retaining sleeve having a rounded end portion and a center longitudinal hole running through the sleeve whereby the stylet wire retaining sleeve is swaged onto the stylet wire and subsequently the stylet wire including the swaged stylet wire retaining sleeve frictionally engages within the longitudinal hole at the inside end of the thin wall stylet knob thereby forming the stylet.

One significant aspect and feature of the present invention is a stylet which is easy to manufacture and assemble, provides for controlled stylet wire length, and more importantly, provides for a straight stylet wire.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the Figures thereof and wherein:

FIG. 1 illustrates a plan view of a stylet, the present invention;

FIG. 2 illustrates a view of the stylet prior to manufacturing assembly, and;

FIG. 3 illustrates a cross sectional view of the stylet holder taken along line 3—3 of FIG. 1.

DETAILED DESCRIPTION OF THE PREFERRED EMBODIMENT

FIG. 1, which illustrates a plan view of a stylet 10, the present invention, shows the stylet 10, a thin wall stylet knob 12 including a ribbed handle 12a and a tapered end 12b, and a stylet wire 14 having a tip 14a.

FIG. 2, which illustrates an unassembled view of the stylet 10 before assembly, shows the stylet knob 12, the stylet wire 14, and a swaged stylet wire retaining sleeve 16 swaged onto the stylet wire 14 as now described in detail in FIG. 3.

FIG. 3, which illustrates a cross-sectional view of the thin walled stylet knob 12, taken along lines 3—3 of FIG. 1, shows the stylet 10 including the thin walled stylet knob 12 having the ribbed handle portion 12a, the tapered end 12b, the inside tapered end 12c, the longitudinal hole 12d running substantially throughout the longitudinal length of the stylet knob 12, and a stylet wire hole 12e. The stylet wire retaining sleeve 16, having a rounded portion 16a, and a hole, 16b, slides over the stylet wire 14 as illustrated in FIG. 2, and is swaged or press fitted onto the stylet wire 14 forming outwardly extended portions 16c and 16d.

PREFERRED MODE OF OPERATION

The stylet 10 is assembled by initially cutting the stylet wire 14 to the desired length and then sliding the stylet wire retaining sleeve 16 over the stylet wire 14 so that the center longitudinal hole 16b engages over the other end of the stylet wire 14.

The stylet wire retaining sleeve 16 is press fitted or swaged over the stylet wire 14 so as to be securely and frictionally engaged thereto by any well-known means.

The stylet wire 14 is inserted through the longitudinal hole 12d of the thin walled stylet knob 12 and subsequently through the end hole 12e as illustrated in FIG. 2.

The stylet wire 14 is pulled through the stylet knob 12 so that the accompanying sleeve 16 slides through the entire length of the longitudinal hole 12d. The swaged sleeve 16 engages against the thin walled interior of the hole 12b until the point that the rounded forward portion 16a of the sleeve engages against the inner end 12c and the swaged ends 16c and 16d engage against and into the stylet at point 12e forming the stylet 10.

Various modifications can be made to the stylet of the present invention without departing from the apparent scope of the present invention.

Having thus described the invention, there is claimed as new and desired to be secured by Letters Patent:

1. A stylet comprising:
    a knob having a proximal end and a distal end and having a longitudinal hole from said proximal end to said distal end wherein said longitudinal hole has a first diameter at said proximal end and a second diameter at said distal end;
    a stylet wire having a proximal end and a distal end and having said proximal end of said stylet wire inserted into said distal end of said longitudinal hole of said knob; and
    a stylet retaining sleeve larger than said second diameter frictionally engaged within said longitudinal hole and frictionally attached to said proximal end of said stylet wire.

2. A stylet according to claim 1 wherein said first diameter is larger than said second diameter.

3. A stylet according to claim 1 or 2 wherein said stylet retaining sleeve frictionally engages said proximal end of said stylet wire by being swaged.

4. A stylet according to claim 3 wherein said stylet wire has a substantially uniform diameter.

* * * * *

UNITED STATES PATENT AND TRADEMARK OFFICE
CERTIFICATE OF CORRECTION

PATENT NO. : 4,253,462
DATED : March 3, 1981
INVENTOR(S) : DUTCHER et al

It is certified that error appears in the above—identified patent and that said Letters Patent are hereby corrected as shown below:

Column 2,
Line 49, after "sleeve" insert --16--.

Signed and Sealed this

Twenty-sixth Day of May 1981

[SEAL]

Attest:

RENE D. TEGTMEYER

Attesting Officer

Acting Commissioner of Patents and Trademarks